(12) United States Patent
Nuthi

(10) Patent No.: US 11,055,838 B2
(45) Date of Patent: Jul. 6, 2021

(54) SYSTEMS AND METHODS FOR DETECTING ANOMALIES USING IMAGE BASED MODELING

(71) Applicant: GE Precision Healthcare LLC, Wauwatosa, WI (US)

(72) Inventor: Sridhar Nuthi, Waukesha, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 28 days.

(21) Appl. No.: 16/707,585

(22) Filed: Dec. 9, 2019

(65) Prior Publication Data

US 2021/0174485 A1    Jun. 10, 2021

(51) Int. Cl.
| G06K 9/00 | (2006.01) |
| G06T 7/00 | (2017.01) |
| G06K 9/62 | (2006.01) |
| G16H 30/40 | (2018.01) |

(52) U.S. Cl.
CPC .......... *G06T 7/0002* (2013.01); *G06K 9/6256* (2013.01); *G06K 9/6262* (2013.01); *G16H 30/40* (2018.01); *G06T 2207/20081* (2013.01); *G06T 2207/30242* (2013.01)

(58) Field of Classification Search
CPC ......... G06T 7/0002; G06T 2207/30242; G06T 2207/20081; G16H 30/40; G06K 9/6256; G06K 9/6262
See application file for complete search history.

(56) References Cited

U.S. PATENT DOCUMENTS

| 2009/0281839 | A1* | 11/2009 | Lynn ..................... G16H 30/40 705/3 |
| 2019/0286942 | A1* | 9/2019 | Abhiram ............... G06N 3/0454 |
| 2019/0355114 | A1* | 11/2019 | Muehlberg ................ G06T 7/11 |
| 2020/0223659 | A1* | 7/2020 | Hikichi .................. B66B 13/02 |
| 2020/0342968 | A1* | 10/2020 | Avinash ................. G06F 9/451 |

* cited by examiner

*Primary Examiner* — Xin Jia
(74) *Attorney, Agent, or Firm* — Andrus Intellectual Property Law, LLP

(57) ABSTRACT

A method for detecting anomalies in a system. The method includes collecting training data from the system, converting the training data into training images using an image generator, and designating each of the training images as corresponding to events for the system, where the events are at least one of an expected normal event and a non-normal event. The method further includes generating an image recognition model based on the training images and the designations thereof. The method further includes collecting new data from the system, converting the new data into input images, and analyzing the input images using the image recognition model to determine which of the events for the system are represented in the input images, where the anomalies are detected when the input images are determined to at least one of represent a non-normal event and fail to represent an expected normal event.

20 Claims, 8 Drawing Sheets

FIG. 4A ially relates to systems and methods for detecting anomalies using image based modeling, and more particularly to systems and methods for detecting anomalies using image based modeling, particularly by converting non-image data to image data for analysis.

SYSTEMS AND METHODS FOR DETECTING ANOMALIES USING IMAGE BASED MODELING

FIELD

The present disclosure generally relates to systems and methods for detecting anomalies using image based modeling, and more particularly to systems and methods for detecting anomalies using image based modeling, particularly by converting non-image data to image data for analysis.

BACKGROUND

Different types of systems presently known in the art, including medical imagining systems, for example, often produce various logs corresponding to applications running within the system, system logs, and diagnostic data. This asset or machine data may then later be used for troubleshooting anomalies within the system, such as by providing a mechanism for determining which subsystem within the system is most likely involved.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to a method for detecting anomalies in a system. The method includes collecting training data from the system, converting the training data into training images using an image generator, and designating each of the training images as corresponding to events for the system, where the events are at least one of an expected normal event and a non-normal event. The method further includes generating an image recognition model based on the training images and the designations thereof. The method further includes collecting new data from the system, converting the new data into input images, and analyzing the input images using the image recognition model to determine which of the events for the system are represented in the input images, where the anomalies are detected when the input images are determined to at least one of represent a non-normal event and fail to represent an expected normal event.

Another embodiment generally relates to a system for detecting anomalies in a medical imaging system. The system includes an image recognition model based on training images converted from training data produced by the system, where the training data represents events occurring in the system, and where the events include at least one of expected normal events and non-normal events. A data aggregator collects and aggregates new data from the system, where the new data also reflect the events occurring in the system. An image generator converts the new data into input images and a computing system analyzes the input images using the image recognition model to determine which of the events for the system are represented in the input images. The anomalies are detected when the input images are determined to at least one of represents one of the non-normal events and fails to represent one of the expected normal events.

Another embodiment generally relates to a method for detecting anomalies in a medical imaging system. The method includes collecting training data from the medical imaging system, converting the training data into training images using an image generator, and designating each of the training images as corresponding to events for the medical imaging system, where the events are at least one of an expected normal event and a non-normal event. The method further includes generating an image recognition model via machine learning based on the training images and the designations thereof. The method further includes collecting new data from the medical imaging system, where the new data includes environmental data for the medical imaging system and logs for applications running on the medical imaging system. The method further includes converting the new data into input images, and identifying a pattern in the new data and modifying the input images corresponding thereto and demarcating the identification of the pattern therein. The method further includes analyzing the input images using the image recognition model to determine which of the events for the system are represented in the input images. The anomalies are detected when the input images are determined to at least one of represent a non-normal event and fail to represent an expected normal event.

Various other features, objects and advantages of the disclosure will be made apparent from the following description taken together with the drawings.

BRIEF DESCRIPTION OF THE DRAWINGS

The present disclosure is described with reference to the following Figures.

FIGS. 4A-4B depict exemplary sub-processes for creating the images as provided in FIG. 3.

DETAILED DISCLOSURE

The present disclosure generally relates to systems and methods for detecting and troubleshooting anomalies within a system of interest (not numbered), such as a medical imaging system like an MRI system or CT system, or a wind turbine, for example. Traditional approaches for determining the root cause for anomalies within a system of interest rely upon complicated data preparation, processing, and analysis that is costly and requires a lot of time. Additionally, the steps of obtaining and preparing this information, as well as conducting the subsequent analysis, typically requires significant expertise and experience to yield reasonable accuracy. In the context of a medical imaging system, any downtime may be very expensive for the owner, resulting in loses of tens of thousands of dollars per hour. The lengthy process of detection and troubleshooting in the manner presently known, as well as any ineffective attempts to resolve such anomalies, become very significant.

Figure 1:
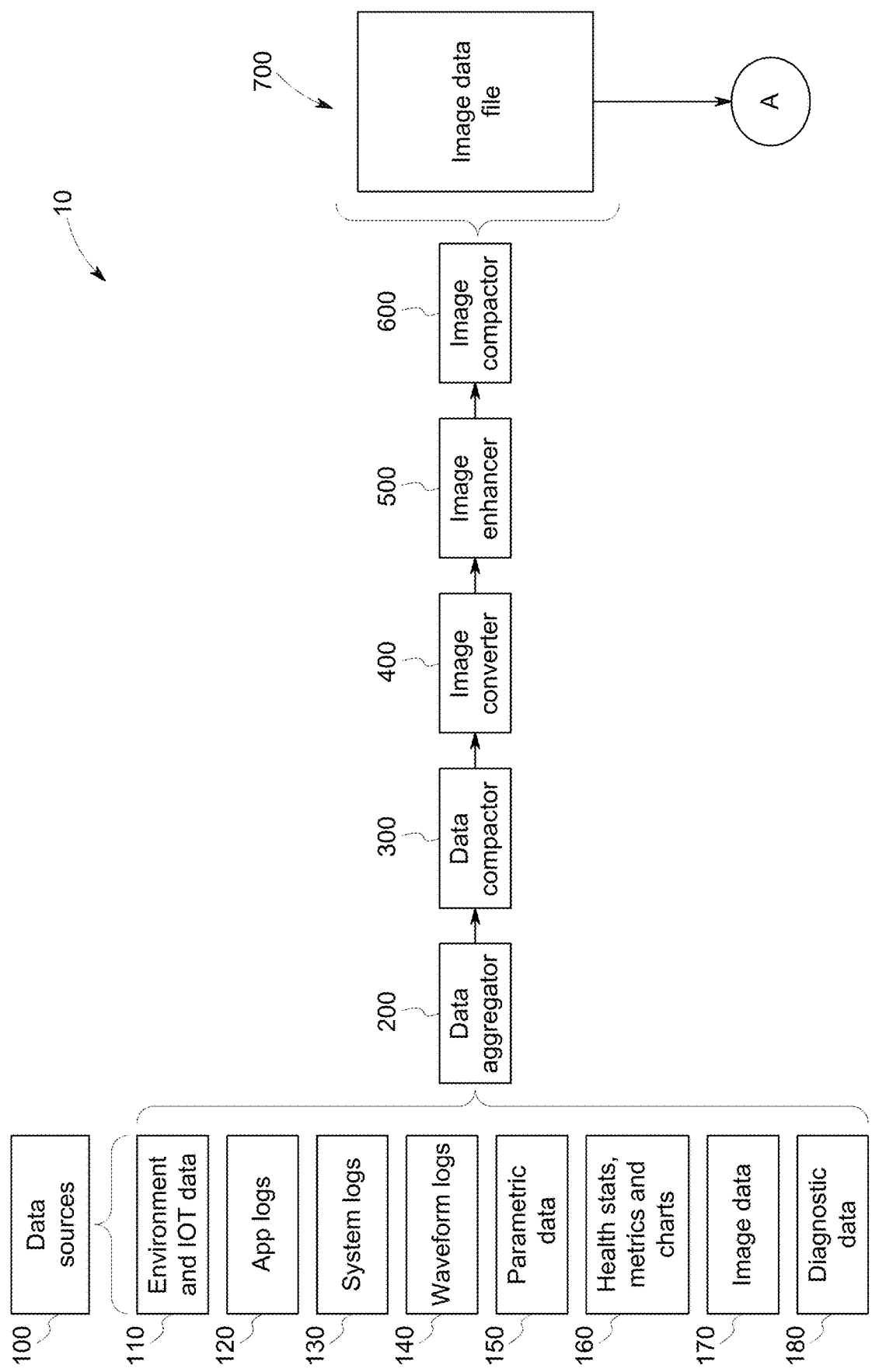
FIGS. 1 and 2 depict and exemplary method for training an applying models for detecting anomalies in the system according to the present disclosure.

As exemplified in FIG. 1, the various data sources 100 available for analysis can be numerous, which is both beneficial in that a rich source of information is available for consideration, but also crippling in the sheer volume of data to be handled and considered. For example, these data sources 100 may include Environmental and Internet of Things (IOT) data, such as the temperature, humidity, and other factors corresponding to the location in which a given system of interest is operating. This Environmental and IOT data 110 may be obtained from the system of interest 1 (see FIG. 8) directly, or via tangential sources, such as a temperature sensor provided in the same room in which the system of interest 1 resides. In certain examples, these tangential sources provide data via an IOT network accessible by the system 10 presently disclosed.

Application logs 120 may also be provided, which provide data corresponding to algorithms running on the system of interest, the management of threads operating, and other applications that are executed in conjunction with operation of the system of interest 1.

System logs 130 may also be provided, which in certain examples provide information relating to the machine health for the system of interest, including its central processing unit (CPU) performance, memory usage. Additional information may relate to various operational states depending on nature of the systems of interest 1, including stand-by modes, various stages of imaging, processing imaging, and/or the like.

Waveform logs 140 may also be provided, which for example may include ECG waveforms when the system of interest 1 is an electrocardiogram machine, as well as power cycle data or other waveforms detected or generated by the system of interest 1.

Parametric data 150 may also be available, which in the context of a medical device as the system of interest 1 may include an $SPO_2$ or heartrate for a patient being monitored by the system of interest 1, or other key value pairs or XML data generated by the system of interest 1 or tangential sources (e.g. via an IOT network as described above).

Health statistics, metrics, and charts 160 may also be provided, such as via a machine watchdog application already operating with the system of interest 1. For example, this may include data from applications monitoring the battery or cache use of the system of interest 1, which may already provide additional internal measures of health for the system of interest 1.

Image data 170 may also be provided, particularly in the context of the system of interest 1 being a medical imaging system or other imaging system. Exemplary data may include DICOM images, various error messages, and/or the like.

Finally, diagnostic data 180 already provided by the system of interest 1 may be provide as a data source 100, which may provide findings and other analysis based on one of the other data sources 100 discussed above, and/or other sources already considered by the system of interest 1.

As discussed above, the inventor has recognized that consideration of these many data sources 100 is challenging, costly, and time intensive, often producing a situation of "analysis paralysis" in detecting presence of an anomaly within the system of interest 1, and a root cause thereof. Accordingly, the inventor has developed the presently disclosed systems and methods for detecting potential anomalies and corresponding root causes, particularly by employing image processing techniques, machine learning, and artificial intelligence (AI). In particular, the inventor has recognized that the adage "a picture is worth a thousand words" should be applied to managing the multitude of information provided by the data sources 100 discussed above. Specifically, images may be used in place of these excesses of words and other information, which may then be modified, stored, and processed using imaging techniques. It will further be recognized that by operating in the image space, the system 10 provides enhanced security as no data can be extracted from the images without specific knowledge regarding their creation.

Figure 2:
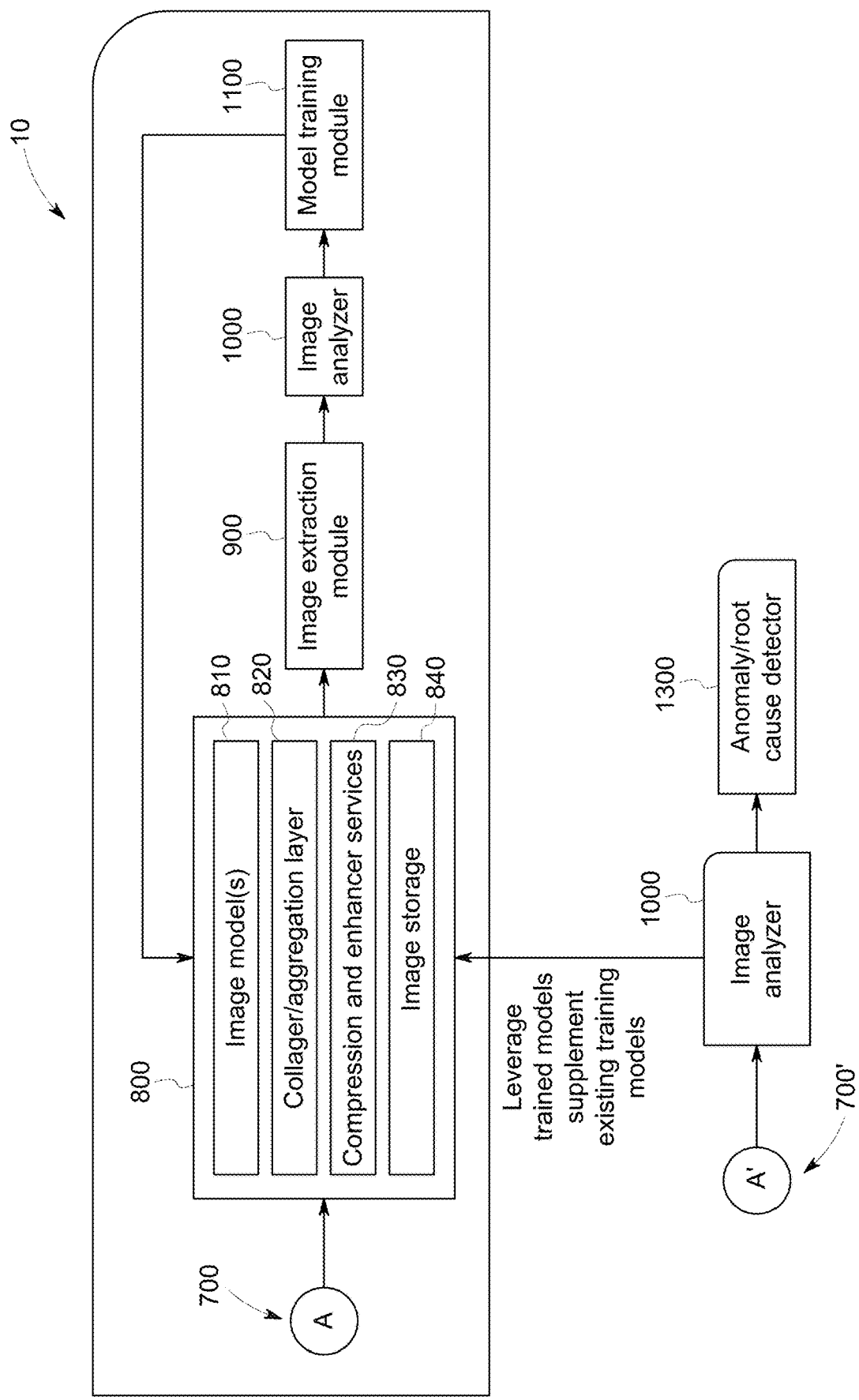

FIGS. 1 and 2 depict an exemplary system 10 for capturing and using the information provided by the data sources 100 to train and subsequently implement models for detecting anomalies within the system of interest 1. In the example shown, the information provided from the various data sources 100 are provided to a data aggregator 200, which collects all of the information into one flow. This aggregation may be completed for one or multiple systems of interest 1, and at different frequencies, such as once per day, once per hour, or other cycles. It will be recognized that the data aggregator 200 is depicted as a module of hardware and/or software configured to execute the functions. Additional information regarding the hardware and software of the system 10 presently disclosed in FIG. 8 and discussed below. The same depictions apply for the other elements of FIGS. 1-2 as well, which will become apparent.

The data outputted by the data aggregator 200 is then received in a data compactor 300, which organizes the aggregated data into a matrix or other structure upfront. The inventor has identified that this assists in better organizing the images generated by the image convertor 400, which receives the outputs from the data compactor 300. The image converter 400 may be provide via custom code written to create images using, for example, a JPEG generator technique or other image format, such as through a bit vector manipulation. In certain embodiments, the image converter 400 may be a text data to image converter already known in the art.

In the system 10 shown, the output of the image converter 400 is then optionally processed with an image enhancer 500. In certain embodiments, the image enhancer 500 uses additional context from the original data sources 100 to parse, analyze, and convert various portions of the image created by the image converter 400 to include visual markups representing this additional context. Exemplary markups may include indicators, metrics, badges, lines, colors, charts, or other information on the image outputted by the image converter 400, which correspond to the known portion of information from the original data source 100. For example, a portion of information from the data sources 100 corresponding to the system of interest starting up may be colored a particular color in a portion of the image created therefrom, and/or a particular shape or symbol may be superimposed on that region of the image. Additional information regarding the image enhancer 500 is also discussed below.

In certain embodiments, output from one or more data sources 100 may be already in image format, pulling the functions of the image convertor 400 upstream in recognition of its integration into a system 10 according to the present disclosure.

Continuing with FIG. 1, the images enhanced by the image enhancer 500 are then be directed to an image compacter 600, which in the present example incorporates a combination of compression and coalition processes to reduce the size or number of overall images. In certain examples, the output of the image compactor 600 is a multi-data source 100 view, or multi-day compilation, for example. In a specific example, images generated by the image convertor 400 once per hour may be combined into six hour segments, thereby providing four compacted images for each day. This may simplify analysis by reducing the number of images consideration, smooth out temporary issues to highlight overall trends (e.g. by averaging these out when the multiple images are combined together), and/or reduce archiving demands.

The output of the image compactor 600 is provided as an image data file 700, which as shown continues with circle A in FIG. 2. This image data file 700 is then fed to a central handler 800, whereby the image data files 700 are incorporated into the image models 810 (discussed further below), incorporated into further collagers and/or aggregation layers 820 similar to that discussed with the image compactor 600, be incorporated in further compression and enhancing similar to that discussed with the image enhancer 500, and/or image storage 400. In the example shown, the image model(s) 810 are initially created and later updated and implemented via modules 900, 1000, and 1100. In one example, the output of the central handler 800, which for example may process image data files 700 taken every six hours for a longer term, such as a week, is then fed to an image extraction module 900, and subsequently an image analyzer 1000. Additional information for the image extraction module 900 and image analyzer are provided below.

The output of the image analyzer 1000 may be then used to train the system 10 with respect to normal versus analogous states using the model training module 1100. This training may be done through, or incorporate machine learning and/or AI technologies known in the art, such as Google®'s TensorFlow, for example. Information is then fed back to the central handler 800 as new information becomes available.

By capturing, organizing, and processing the images as provided in FIGS. 1 and 2, the present system 10 provides that standard image recognition algorithms presently known in the art may be used for analyzing the processed images for the detection of anomalies as presently disclosed. Alternatively, custom image recognition algorithms may also be provided in the model training module 1100, for example.

Figure 5:
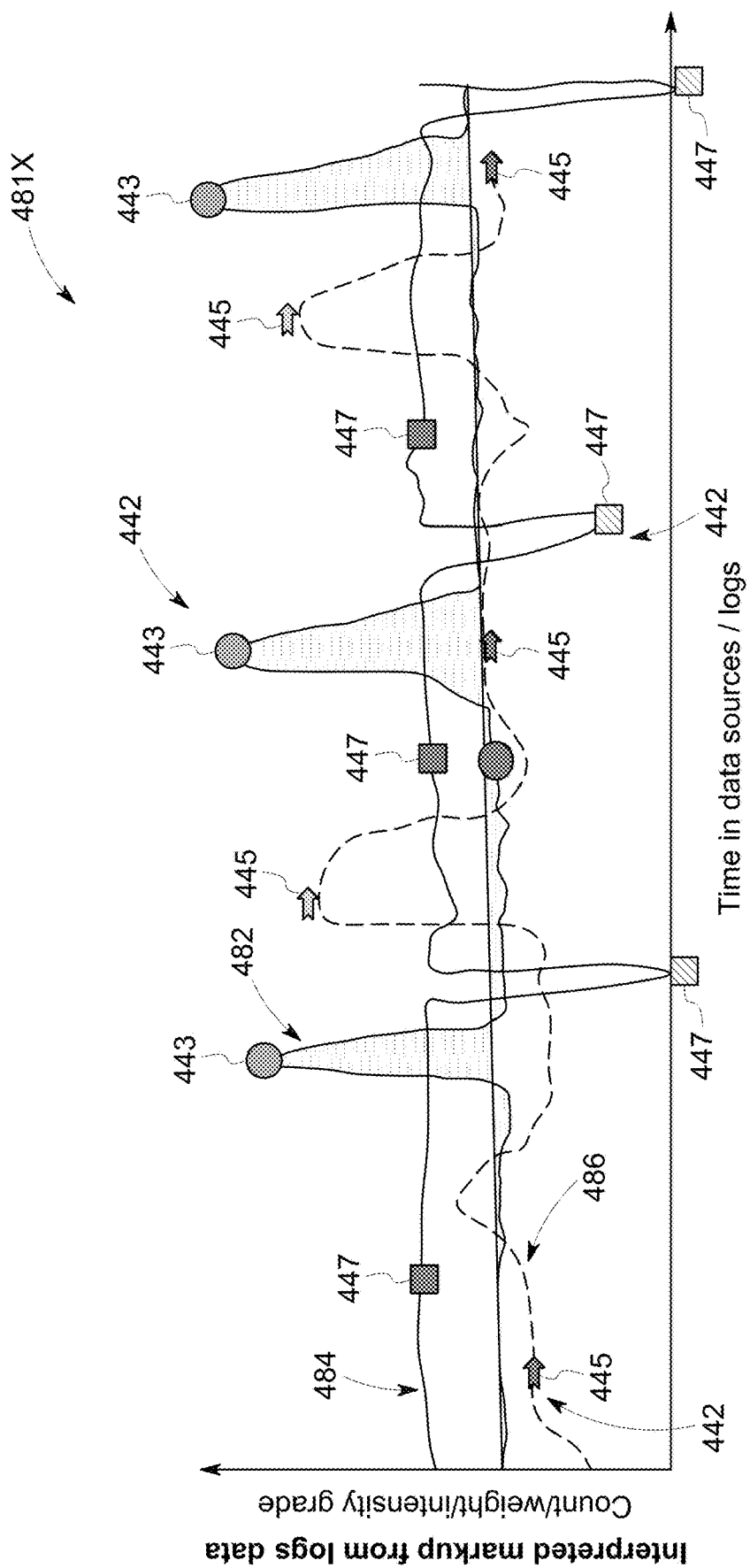
FIG. 5 depicts an exemplary summary generated from the analysis of images using the process of FIG. 3.

It will be recognized that by further applying self-learning algorithms and artificial intelligence, creation of the image data file 700 may also be improved, such as by identifying consistent lines or patterns within the data sources 100, then incorporating unique markups corresponding to specific states identified in the data sources 100 provided as markups by the image enhancer 500. As shown in FIG. 5, the combination of icons, such as markups 422, in a time dimension can quickly tell the story of how the health of the system of interest changes over time or through different system states. Additional discussion of FIG. 5 is provided below.

Returning to FIG. 2, it will be recognized that once the image model 810 has been generated, further improvement to the image model 810 may nonetheless be provided over time. For example, new image data files 700' created after the initial training of the image model 810 may be fed into the presently disclosed system 10 to be assessed via the image analyzer 1000, which may both apply the image model 810 and also update the image model 810 via machine learning, to ultimately detect anomalies via an anomaly and root cause detector 1300. Additional information about identifying anomalies and root causes is provided below.

Figure 3:
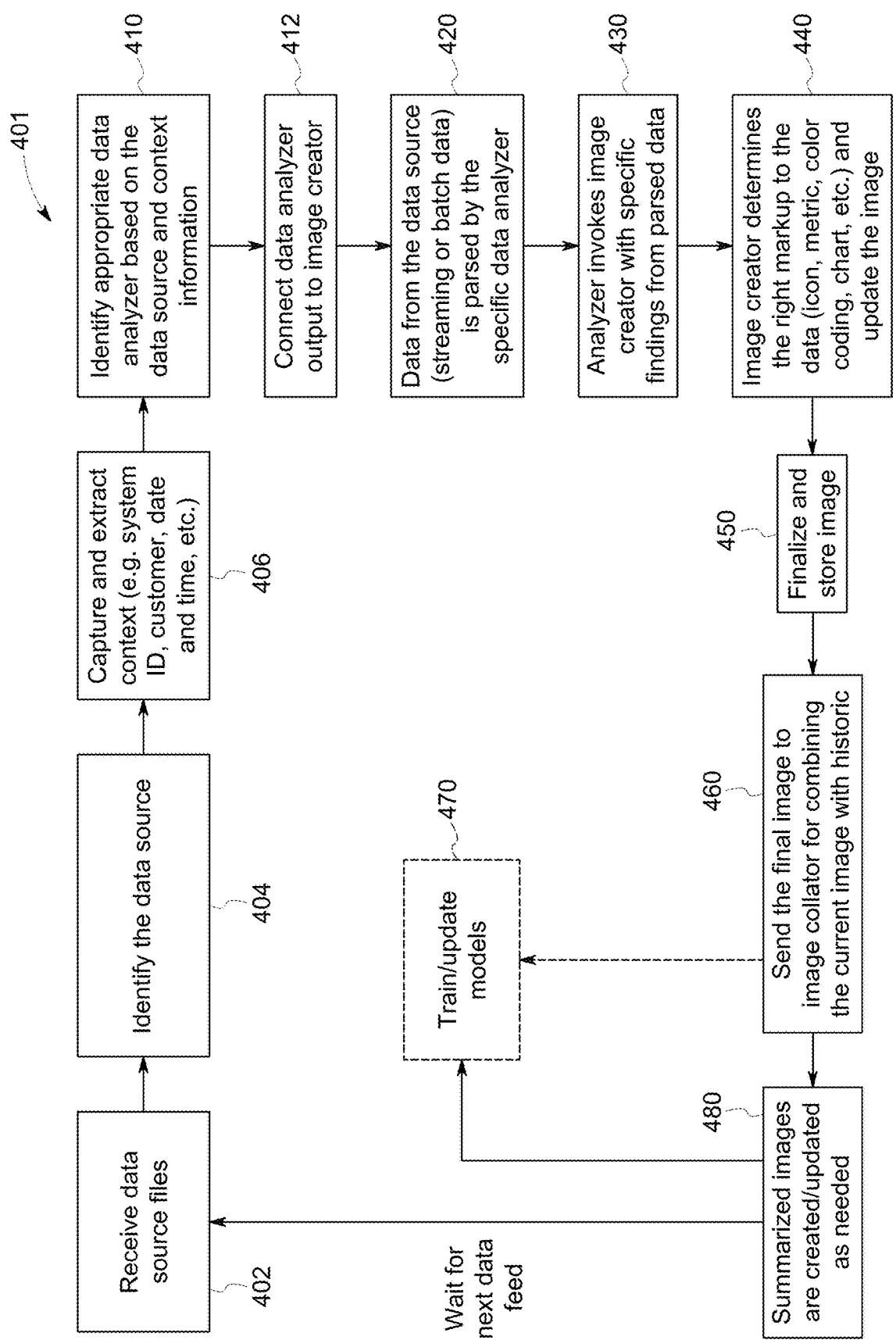
FIG. 3 depicts an exemplary process flow for creating images for training or analysis on the model as may be incorporated within process flow of FIGS. 1 and 2.

FIG. 3 depicts an exemplary method 401 that may be employed by the image converter 400 of FIG. 1. The method 401 begins with receiving data source files in step 402, the origins or sources of which are then identified in step 404. It should be recognized that in the case where only one data source 100 is received in step 402, the identity of the data source 100 will be known and thus step 404 would be unnecessary. The context for each of the incoming data source files is then captured and extracted, such as a system ID for the system of interest 1, customer information, date and time information, and the like in step 406. The method 401 then includes identifying an appropriate data analyzer in step 410 for analyzing the data source files based on the particular data source identified in step 404, as well as the context information identified in step 406. Output from the appropriate data analyzer of step 410 is then provided in step 412 to the image convertor 400, which as previously described may be a text to image converter presently known in the art, or a custom program particularly suited for data corresponding to the system of interest 1. It will be recognized that data from the data sources 100 need not be only text or images. For example, the inventor has identified that audio files are well-suited for conveying noise data.

Data from the data source received in step 402 is the further parsed by the specific data analyzer in step 420, which is used to identify enhancements for the specific findings of the parse data in step 430, and ultimately to provide corresponding markups to the image in step 440. This may be similar to the descriptions above corresponding to the functions performed by the image enhancer 500, also shown in FIG. 1. The finalized image is stored in step 450, and in the present example is further sent for collating and/or collaging in step 460 to combine the latest image from step 450 with historic images previously collected. The final image combined in step 460 is then used to train and update the models in step 470, and also used to generate summarized images in step 480, which are discussed further below. From there, the process 401 repeats in a closed loop fashion as new data source files are once again received in step 402.

Figure 4A:
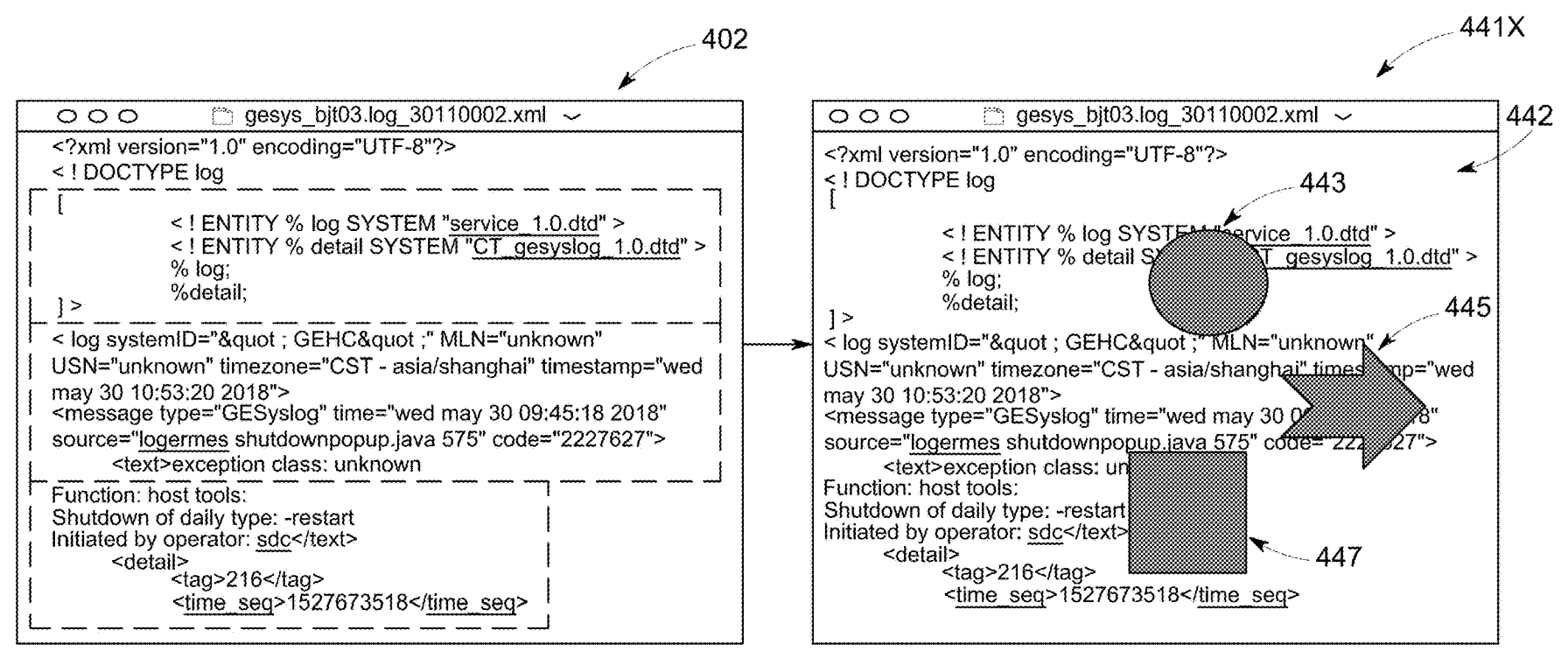
Figure 4B:
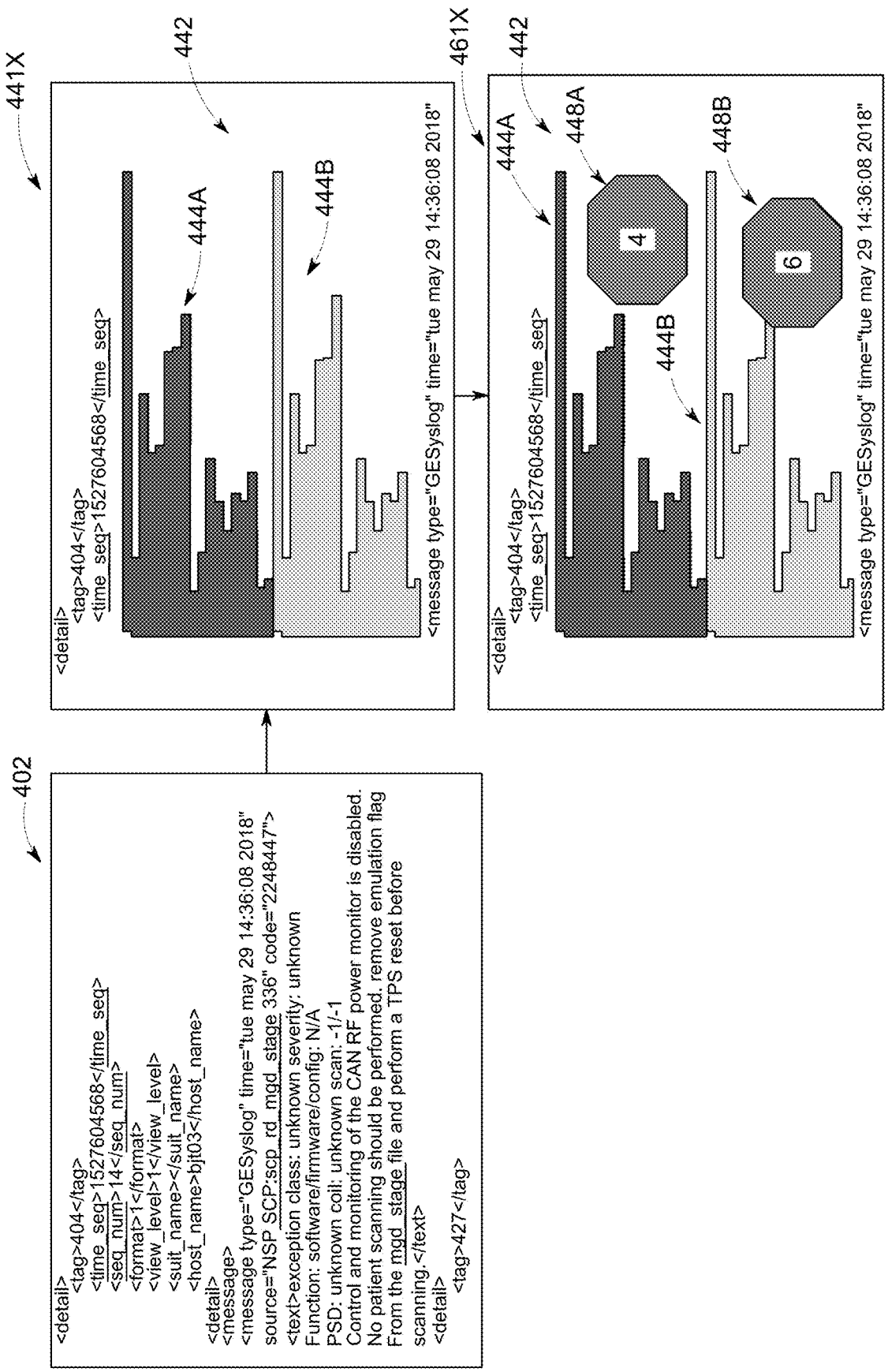

FIGS. 4A and 4B provide exemplary output for some of the steps discussed above with respect to FIG. 3. In particular, FIG. 4A depicts an exemplary marked-up image 441X following the completion of step 440 from FIG. 3, namely the incorporation of markups 442 within the image. In the example shown, three specific icons have been identified through patterns recognized in the original data source files received from step 402: a first icon 443, second icon 445, and third icon 447. By providing these icons as markups 442 within the marked up image 441X, systemic or repeated portions of information can be readily identifiable and patterns quickly highlighted within large volumes of data.

FIG. 4B depicts an alternative marked up image 441X, whereby the markups 442 corresponding to segments of the information within the data source files received in step 402 are color coded rather than having an icon superimposed thereon. In the example shown, a first pattern 444A is colored or shaded in a first manner, and a second pattern 444B is colored or shaded in another manner distinguishable from the first pattern 444A. The example of FIG. 4B further shows the generation of an exemplary combined image 461X based on a compilation of multiple images finalized and stored in step 450 of FIG. 3. Specifically, the exemplary combined image 461X provides the markups 442 from the exemplary marked up image 441X previously discussed, but now also incorporates a first count 448A reflecting the number of times the first pattern 444A is present in the combined image 461X, as well as a second count 448B corresponding to the second pattern 444B. In this manner, an operator or machine learning device may quickly discern the prevalence of particular patterns within the data, which the inventor has identified to be instrumental in identifying anomalies and the root causes thereof.

In addition, the markups 442 of FIGS. 4A and 4B may be further used to generate summary images 481X, such as those discussed with respect to FIG. 3 in step 480, which is shown in FIG. 5. In the example shown, a time-based plot is generated corresponding to three metrics of interest: system usage 482, system status 484, and system health 486. In this example, any markups 442 identified within the marked-up images 441X (FIGS. 4A and 4B) are shown on the plot at the corresponding time, whereby first icons 443 are shown and correspond to system usage 482, second icons 445 are shown and corresponds to system health 446, and third icons 447 provided corresponding with system status 484. It should further be noted that the markups 442 may provide information above and beyond the generally shape thereof, including colors, shading, and line hashing, for example. By providing the exemplary summarized image 481X of FIG. 5, an analyst can quickly see the frequency of conditions corresponding to the markups 442 over time, and any changes in behavior.

Figure 6:
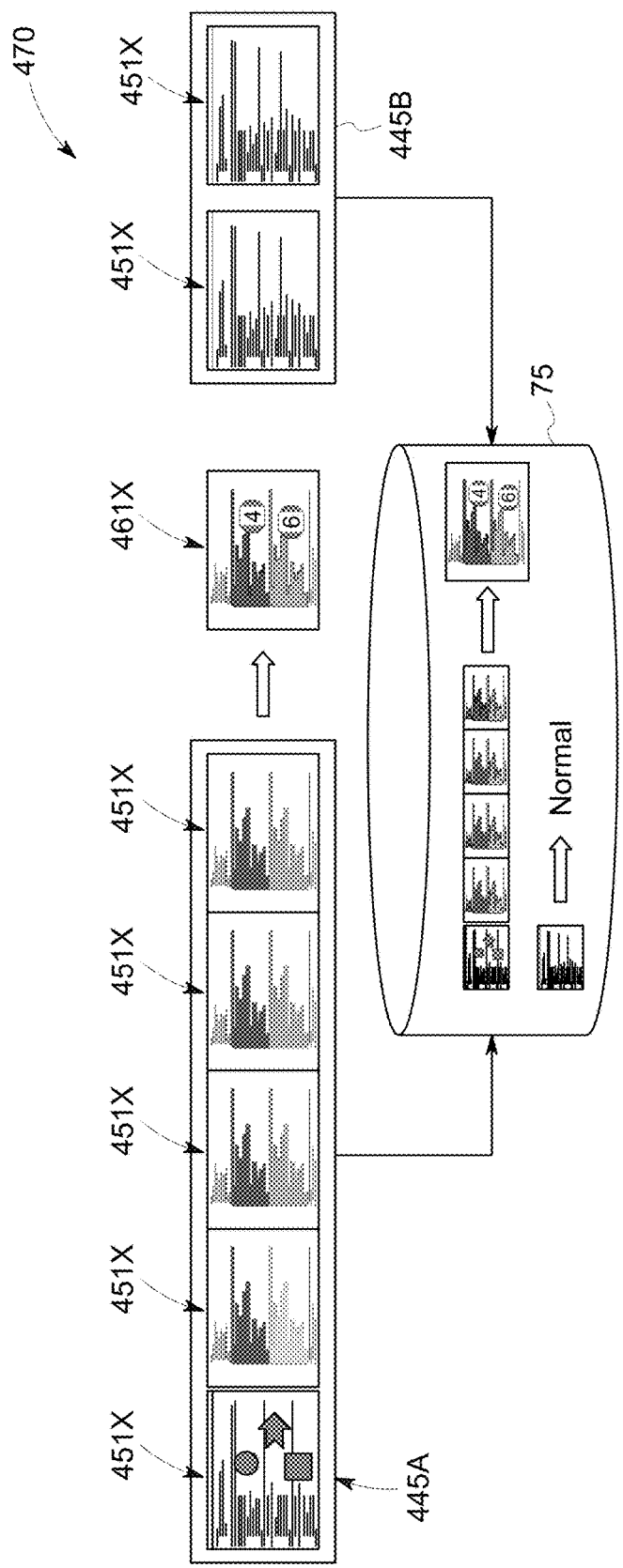
FIG. 6 depicts an exemplary process flow for updating the training model shown in FIG. 3.

FIG. 6 provides additional exemplary information with respect to the training and updating of modules in step 470 as described above and shown in FIG. 3. In the example shown, exemplary final images 451X stored in step 450 are identified as corresponding to a first pattern 445A (which may be a pattern, or pattern of patterns as previously described) and stored as such within the model repository 75. This may also include any further processing of the final images 451X, in this case an exemplary combined image 461X generated at step 460 and the process 401 shown in FIG. 3. In this manner, all of the information corresponding to the first pattern 445A and exemplary combined images 461X thereof are associated with a certain condition, in this case identified as corresponding to a normal condition within the image model 810 stored in the model repository 75. As also depicted in FIG. 6 are two additional final exemplary final images 451X identified as corresponding to a second pattern 445B, and likewise stored in the image model 810 within the model repository 75. This second pattern 445B may also be identified as corresponding to a normal condition for the system of interest, or may identify or may be labeled as corresponding to a particular anomaly or failure mode, such as a failed or failing x-ray tube in the context of a medical imaging system, for example.

Figure 7:
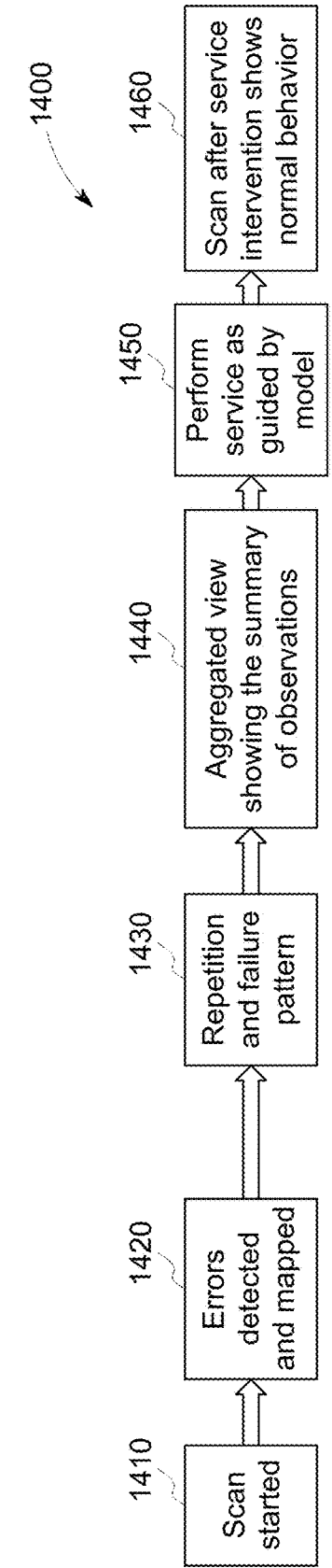
FIG. 7 depicts an exemplary process flow for detecting an anomaly and confirming correction thereof according to the present disclosure.

FIG. 7 summarizes the overall method 1400 for the systems 10 and methods previously discussed for detecting, and confirming resolution of, an anomaly within the system of interest. In the example of a medical imaging system, a scan is started in step 1410, whereby errors and patterns corresponding to normal and abnormal conditions are detected and mapped in step 1420, using the methods and systems 10 previously discussed. These include identification of repeated failure patterns in step 1430, which are then aggregated in step 1440 for analysis, such as the generation of summarized images in step 480 as discussed above with respect to FIG. 3. Services are then provided (e.g. by a trained technician) as guided by the model 1800 in step 1480, such as the replacement of an x-ray tube in the example discussed above. The method 1400 then continues with once again performing a scan in step 1460, whereby the subsequent scan is then determined to correspond to normal behavior, and thus indicate that the system of interest has been restored to health. This information may be further fed to update the image model 810 or root cause map 77 (FIG. 8, discussed below) in step 470 of FIG. 3 as discussed above, strengthening the prediction of the service suggested to be performed in step 1450. Likewise, if the scan conducted in step 1460 does not yield a corresponding indication that the anomaly has been resolved, this information is also provided to the image model 810 and root cause map 77 and, through machine learning and artificial intelligence, improves each for future recognition of anomalies.

Figure 8:
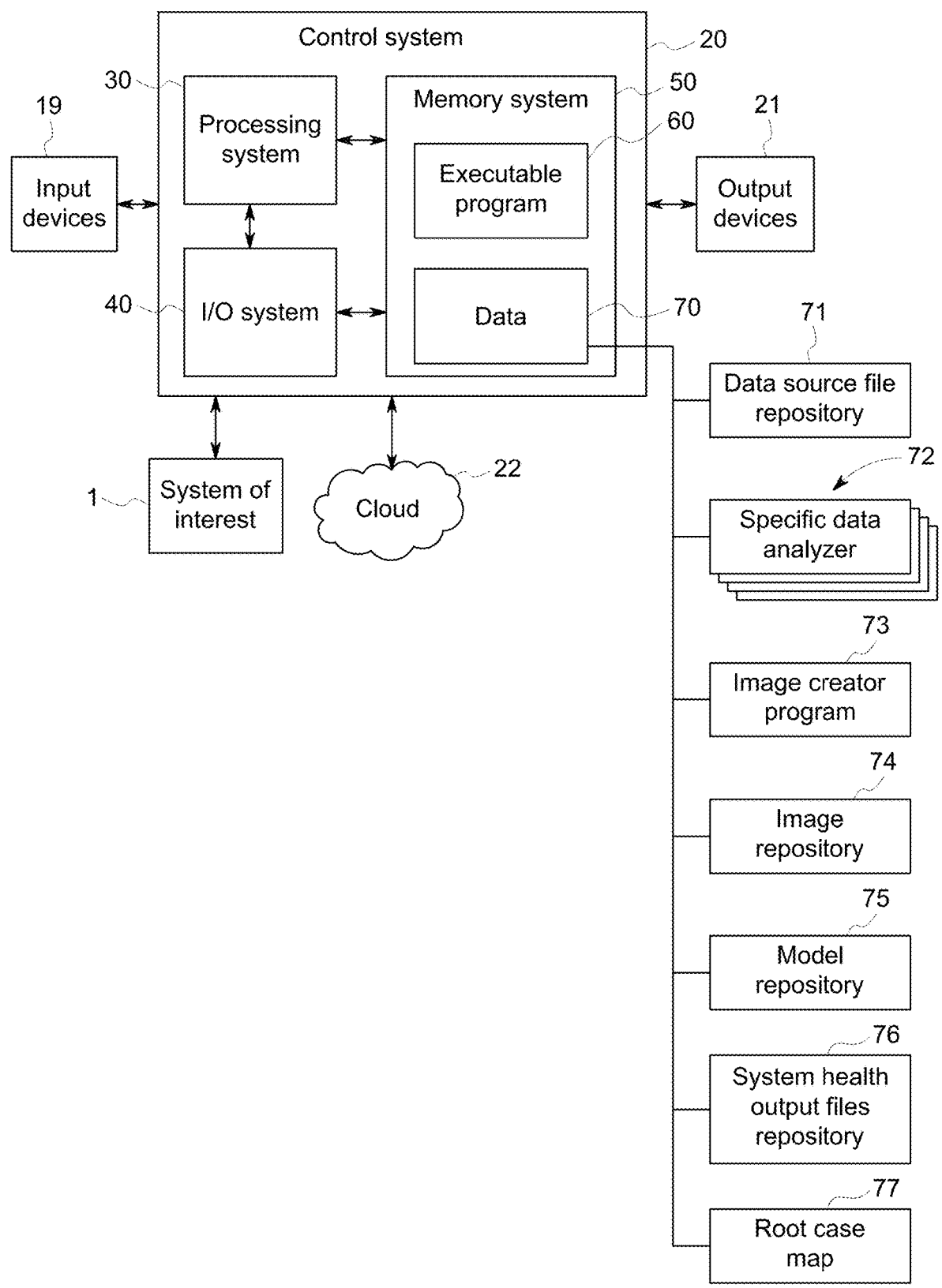
FIG. 8 depicts an exemplary control system for detecting anomalies using images according to the present disclosure.

FIG. 8 depicts an exemplary control system 20 operatively coupled within the system 10 for performing the functions discussed above. Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

The control system 20 may be a computing system that includes a processing system 30, memory system 50, and input/output (I/O) system 40 for communicating with other devices, such as input devices 19 (e.g., data sources 100) and output devices 21, either of which may also or alternatively be stored in a cloud 22. The system of interest 1 is shown separately as it may constitute both an input device 19 and an output device 21, depending upon the particular configuration of the system 10. The processing system 30 loads and executes an executable program 60 from the memory system 50, accesses data 70 stored within the memory system 50, and directs the system 10 to operate as described in further detail below.

The processing system 30 may be implemented as a single microprocessor or other circuitry, or be distributed across multiple processing devices or sub-systems that cooperate to execute the executable program 60 from the memory system 50. Non-limiting examples of the processing system include general purpose central processing units, application specific processors, and logic devices.

The memory system 50 may comprise any storage media readable by the processing system 30 and capable of storing the executable program 60 and/or data 70. The memory system 50 may be implemented as a single storage device, or be distributed across multiple storage devices or sub-systems that cooperate to store computer readable instructions, data structures, program modules, or other data. The memory system 50 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

The data 70 may store a wide variety of information, including a data source file repository 71 for storing information from the various data sources 100 and processed versions thereof. Specific data analyzers 72 may also be started within the data 70, which proved for particular processing of the data sources 100 stored within the data source file repository 71. The image creator program 73 may also be stored in the data 70, as well as an image repository 74 for storing individual, marked-up, and/or combined images, as well as summarized images produced through the various steps disclosed above. A model repository 75 is also provided for storing one or more image models 810 as discussed above, as is a system health output files repository 76, which may for example store information relating to the confirmation of service steps resolving an identified anomaly. In certain examples, a root cause map 77 is also stored as a distinct file within the data 70, which may provide further information to the image model 810 for identifying root causes based on anomalies detected within the system of interest 1. This root cause map 77 may initially be provided as a lookup table or other structure correlating probably root causes based on symptoms (e.g. anomalies). However, the root cause map 77 may be a living file, updated intelligently over time for a particular system of interest 1, or across an entire network of such devices via the cloud 102, for example.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A method for detecting anomalies in a system, the method comprising:
    collecting training data from the system;
    converting the training data into training images using an image generator;
    designating each of the training images as corresponding to events for the system, wherein the events are at least one of an expected normal event and a non-normal event;
    generating an image recognition model based on the training images and the designations thereof;
    collecting new data from the system;
    converting the new data into input images; and
    analyzing the input images using the image recognition model to determine which of the events for the system are represented in the input images;
    wherein the anomalies are detected when the input images are determined to at least one of represent a non-normal event and fail to represent an expected normal event.

2. The method according to claim 1, wherein the training data and the new data include system logs generated during operation of the system.

3. The method according to claim 1, further comprising identifying a pattern in at least one of the training data and the new data and modifying an at least one of the training images and the input images corresponding thereto to demarcate the identification of the pattern therein.

4. The method according to claim 3, wherein the modification is color coding.

5. The method according to claim 3, wherein the pattern corresponds to the system starting up.

6. The method according to claim 3, further comprising counting a number of times the pattern is identified over a period of time.

7. The method according to claim 1, further comprising identifying a pattern in at least one of the training data and the new data, and further comprising removing the pattern from at least one of the training data and the new data prior to converting into the training images and the input images, respectively.

8. The method according to claim 1, wherein the image recognition model is generated via machine learning.

9. The method according to claim 8, further comprising updating the image recognition model by adding a portion of the new data to the training data.

10. The method according to claim 9, wherein the machine learning process is supervised such that user feedback is used to designate the events corresponding to the portion of the new data being added to the training data.

11. The method according to claim 1, further comprising identifying probable root causes for the anomalies detected.

12. The method according to claim 11, further comprising determining when system changes are made, and further comprising determining whether the system changes resolve the anomalies detected.

13. The method according to claim 12, wherein the probable root causes are stored in a root case database, further comprising updating the probably root causes database based on the determination of whether the system changes resolved the anomalies detected.

14. The method according to claim 1, further comprising trending changes in at least one of the training images and the input images over time.

15. The method according to claim 1, wherein each of the input images represents the new data generated by the system over one day, and wherein multiple of the input images are combined analyzing together using the image recognition model.

16. The method according to claim 1, wherein the new data is in text form.

17. The method according to claim 1, wherein the system is a medical imaging system that produces imaging data, and wherein the training data and the new data include the imaging data produced by the medical imaging system.

18. The method according to claim 1, further comprising identifying an experiment expected to impact the new data produced by the system for testing the image recognition model, and further comprising changing the system according to the experiment and updating the image recognition model according to the impact thereof.

19. A system for detecting anomalies in a medical imaging system, the system comprising:

an image recognition model based on training images converted from training data produced by the system, wherein the training data represents events occurring in the system, and wherein the events include at least one of expected normal events and non-normal events;

a data aggregator that collects and aggregates new data from the system, wherein the new data also reflect the events occurring in the system;

an image generator that converts the new data into input images;

a computing system that analyzes the input images using the image recognition model to determine which of the events for the system are represented in the input images;

wherein the anomalies are detected when the input images are determined to at least one of represents one of the non-normal events and fails to represent one of the expected normal events.

20. A method for detecting anomalies in a medical imaging system, the method comprising:

collecting training data from the medical imaging system;

converting the training data into training images using an image generator;

designating each of the training images as corresponding to events for the medical imaging system, wherein the events are at least one of an expected normal event and a non-normal event;

generating an image recognition model via machine learning based on the training images and the designations thereof;

collecting new data from the medical imaging system, wherein the new data includes environmental data for the medical imaging system and logs for applications running on the medical imaging system;

converting the new data into input images;

identifying a pattern in the new data and modifying the input images corresponding thereto and demarcating the identification of the pattern therein; and analyzing the input images using the image recognition model to determine which of the events for the system are represented in the input images;

wherein the anomalies are detected when the input images are determined to at least one of represent a non-normal event and fail to represent an expected normal event.

* * * * *